United States Patent [19]

Rivier et al.

[11] 4,211,693

[45] Jul. 8, 1980

[54] PEPTIDES WITH PARA-SUBSTITUTED PHENYLALANINE

[75] Inventors: Jean E. F. Rivier; Marvin R. Brown; Wylie W. Vale, Jr., all of La Jolla, Calif.

[73] Assignee: The Salk Institute for Biological Studies, San Diego, Calif.

[21] Appl. No.: 967,505

[22] Filed: Dec. 7, 1978

Related U.S. Application Data

[63] Continuation-in-part of Ser. No. 834,221, Sep. 20, 1977, abandoned.

[51] Int. Cl.$^2$ .................... C07C 103/52; A61K 37/00
[52] U.S. Cl. ............................... 260/112.5 S; 424/177
[58] Field of Search .................. 424/177; 260/112.5 S

[56] References Cited

U.S. PATENT DOCUMENTS

| | | | |
|---|---|---|---|
| 4,011,207 | 3/1977 | Sarantakis | 260/112.5 S |
| 4,062,816 | 12/1977 | Shields | 260/112.5 S |
| 4,066,827 | 1/1978 | Seita et al. | 260/112 R |
| 4,093,574 | 6/1978 | Shields | 260/112.5 S |
| 4,105,603 | 8/1978 | Vole, Jr. et al. | 260/112.5 S |
| 4,115,554 | 9/1978 | Veber | 260/112.5 S |

OTHER PUBLICATIONS

Rivier et al., J. Med. Chem. 1976, 19, 1010-1013.

*Primary Examiner*—Delbert R. Phillips
*Attorney, Agent, or Firm*—Fitch, Even & Tabin

[57] ABSTRACT

Somatostatin peptides are modified by substitution of para-methoxylated Phe or para-halogenated Phe for any Phe in the peptide. The modified somatostatin peptide analogs have the formulae:

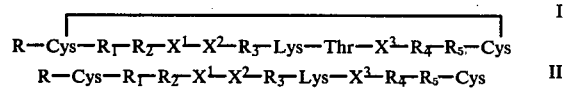

wherein R is hydrogen or an acyl group; $R_1$ is selected from the group consisting of Lys or Des $R_1$; $R_2$ is selected from the group consisting of Asn, Ala or Des $R_2$. The amino acids of the $R_2$ group can be either the L-form or the D-form; $R_3$ is selected from the group consisting of Trp or D-Trp; $R_4$ is selected from the group consisting of Thr or Des $R_4$; $R_5$ is selected from the group consisting of Ser, D-Ser, Phe, X or Des $R_5$; and X is selected from the group consisting of Phe, para-halogenated Phe and para-methoxylated Phe. Provided that at least one X is either para-halogenated Phe or para-methoxylated Phe.

9 Claims, No Drawings

PEPTIDES WITH PARA-SUBSTITUTED PHENYLALANINE

The invention described herein was made in the course of work under a grant or award from the Department of Health, Education, and Welfare.

The present application is a continuation-in-part of application Ser. No. 834,221, filed Sept. 20, 1977 now abandoned.

The present invention relates generally to modified somatostatin peptides having inhibitory influence on (1) secretion of growth hormone by the pituitary gland, (2) secretion of glucagon and insulin by the pancreas, (3) secretion of vasoactive intestinal polypeptides, secretin, gastrin, and gastric acid secretion in humans and animals. More particularly, the present invention is directed to peptides which are as effective as somatostatin and known somatostatin analogs to inhibit the release of growth hormone by the pituitary gland, but are substantially more potent in their ability to inhibit the release of glucagon and/or insulin by the pancreas.

Somatostatin, the linear form of somatostatin (dihydrosomatostatin) and various acylated derivatives of somatostatin and dihydrosomatostatin are described in U.S. Pat. No. 3,904,595 to Guillemin et al. Somatostatin is a tetradecapeptide and has the following structure, with amino acid moieties numbered from left to right in accordance with usual nomenclature.

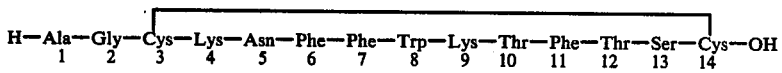

H—Ala—Gly—Cys—Lys—Asn—Phe—Phe—Trp—Lys—Thr—Phe—Thr—Ser—Cys—OH
   1    2    3    4    5    6    7    8    9   10   11   12   13   14

United States Patent Application, Ser. No. 675,149, filed Apr. 8, 1976, describes further somatostatin analogs wherein substitutions for amino acid moieties in the backbone of somatostatin and dihydrosomatostatin provide a peptide which is therapeutically valuable when introduced, either directly or indirectly, into the blood stream of mammals to inhibit the secretion of growth hormone from the pituitary gland and insulin and glucagon from the pancreas. These peptides have D-Trp substituted for Trp in the eight position of somatostatin and may have Ala or Des Asn in the five position.

United States Patent Application, Ser. No. 785,533, filed Apr. 7, 1977, now U.S. Pat. No. 4,133,782, describes other analogs of somatostatin and dihydrosomatostatin which possess dissociated biological activity in respect to the inhibition of growth hormone, insulin or glucagon secretion. These peptides having specific biological activity in respect to release of growth hormone, insulin and glucagon are: des-Asn[5]-[D-Trp[8]]-SS; des-Asn[5]-[D-Trp[8]]-DHSS; [D-Ser[13]]-SS; [D-Ser[13]]-DHSS; [D-Trp[8]]-[D-Ser[13]]SS; [D-Trp[8]]-[D-Ser[13]]DHSS; [D-Cys[14]]-SS; [D-Cys[14]]-DHSS; [D-Trp[8]]-[D-Cys[14]]SS and [D-Trp[8]]-[D-Cys[14]]DHSS.

U.S. Pat. No. 4,105,603, describes peptides having fewer amino acid components than somatostatin and dihydrosomatostatin, but which still possess biological activity in respect to the inhibition of growth hormone, insulin or glucagon secretion. Some of these peptides have dissociated activity. The peptides of this application are defined by the formulae:

Cys—R$_1$—Phe—Phe—R$_2$—Lys—R$_3$—Phe—R$_4$—R$_5$—Cys    I

Cys—R$_1$—Phe—Phe—R$_2$—Lys—R$_3$—Phe—R$_4$—R$_5$—Cys    II where R$_1$ is selected from Asn and des R$_1$, R$_2$ is selected from Trp and D-Trp, R$_3$ is selected from Phe and Thr, R$_4$ is selected from Thr and des R$_4$, and R$_5$ is selected from Ser, Phe, and des R$_5$ provided that at least one of R$_1$, R$_4$, and R$_5$ is deleted.

From the foregoing discussion of the somatostatin art it is apparent that a vast number of somatostatin analogs have been developed. These analogs have various potencies, relative to somatostatin, in respect to inhibition of release of growth hormone, glucagon, insulin, vasoactive intestinal polypeptides, secretion, gastrin and gastric acid in warm blooded animals. The novel peptides of the present invention are based on the discovery that para-halogenated Phe or para-methoxylated Phe can be substituted for any Phe in any of the known somatostatin analogs to provide modified somatostatin peptides. The modified peptides either retain their potency in respect to inhibition of release of growth hormone, insulin and glucagon or provide a dissocated effect in respect to inhibition of release of glucagon and insulin.

The novel somatostatin analog peptides of the present invention are defined by the formulae:

R—Cys—R$_1$—R$_2$—X—X—R$_3$—Lys—Thr—X—R$_4$—R$_5$—Cys    I

R—Cys—R$_1$—R$_2$—X—X—R$_3$—Lys—Thr—X—R$_4$—R$_5$—Cys    II where R is hydrogen or an acyl group selected from the group consisting of (a) an amino acid, for the bridge peptides it is preferred that the amino acid does not contain a sulfhydryl group (b) a dipeptide produced from any two amino acids wherein the second amino acid connected to Cys does not contribute stearic hindrance, preferred second amino acids are Gly, Ala and D-Ala, for the bridged peptides it is preferred that the amino acids of the dipeptides do not contain a sulfhydryl group; (c) a tripeptide wherein the third amino acid connected to Cys$_3$ does not contribute stearic hindrance and wherein the remaining two amino acids are any amino acid, preferred third amino acids for the tripeptide are Gly, Ala and D-Ala; for bridged peptides it is preferred that none of the amino acids of the tripeptide contain a sulfhydryl group; (d) a pentapeptide wherein the first three amino acid components are Gly, the fourth amino acid is selected from Ala and D-Ala and the fifth amino acid connected to Cys$_3$ does not contribute stearic hindrance and is selected from Ala, Gly and D-Ala; and (e) aliphatic, aromatic, and cyclic organic acids, other than amino acids, having from one to ten carbon atoms. The organic acids can be saturated and/or can contain other functional groups when R is hydrogen, Cys$_3$ can be des-amino Cys.

Particularly preferred acyl groups for R are selected from the group consisting of Gly, Ala, Ala-Gly, Acetyl-Ala-Gly, Tyr-Gly, Sarc-Gly, Tyr-Ala-Gly, Ala-Tyr-Gly, Gly-Gly-Gly-Ala-Ala, Gly-Gly-Gly-Ala-Gly, Gly, Gly, Gly-Ala-D-Ala, Gly, Gly, Gly-D-Ala-Ala, Gly, Gly, Gly-D-Ala-Gly, Gly, Gly, Gly-D-Ala-D-

Ala, Acetyl, Acryl, Pivayl and Benzoyl. Any of the amino acids of the R group having isomeric forms can be either the L-form or the D-form;

$R_1$ is selected from the group consisting of Lys and Des $R_1$;

$R_2$ is selected from the group consisting of Asn, Ala and Des $R_2$. The amino acids of the $R_2$ group can be either the L-form or the D-form;

$R_3$ is selected from the group consisting of Trp and D-Trp;

$R_4$ is selected from the group consisting of Thr or Des $R_4$;

$R_5$ is selected from the group consisting of Ser, D-Ser, Phe, X or Des $R_5$, and each of $X^1$, $X^2$ and $X^3$ is selected from the group consisting of Phe, para-halogenated Phe and para-methoxylated Phe;

provided that at least one X is either para-halogenated Phe or para-methoxylated Phe.

The nomenclature used to describe peptides in the present specification is in accordance with conventional practice using the first three letters of the trivial name. Also, in accordance with such practice, it is the L-form of the amino acid that is intended, unless otherwise expressly indicated. In this connection it should be understood that either of the Cys amino acid moieties can be either D-Cys or L-Cys.

Pharmaceutically acceptable acid addition salts of the peptides are also within the scope of the present invention. Such acid addition salts include but are not limited to chloride, hydrobromide, sulphate, phosphate, maleate, acetate, citrate, benzoate, succinate, maleate, ascorbate, tartrate and the like.

Also considered to be within the scope of the present invention are intermediates of the formula:

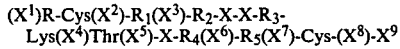
$(X^1)R\text{-}Cys(X^2)\text{-}R_1(X^3)\text{-}R_2\text{-}X\text{-}X\text{-}R_3\text{-}$
$Lys(X^4)Thr(X^5)\text{-}X\text{-}R_4(X^6)\text{-}R_5(X^7)\text{-}Cys\text{-}(X^8)\text{-}X^9$ wherein: $X^1$ is either hydrogen or an α-amino protecting group. The α-amino protecting groups contemplated by $X^1$ are those known to be useful in the art in the step-wise synthesis of polypeptides. Among the classes of α-amino protecting groups covered by $X^1$ are (1) acyl type protecting groups such as formyl, trifluoroacetyl, phthalyl, toluenesulfonyl (tosyl), benzensulfonyl, nitrophenylsulfenyl, tritylsulfenyl, o-nitrophenoxyacetyl, chloroacetyl, acetyl, y-chlorobutyrul, etc; (2) aromatic urethan type protecting groups such as benzyloxycarbonyl and substituted benzyloxycarbonyl such as p-chlorobenzyloxycarbonyl, p-nitrobenzyloxycarbonyl, p-bromobenzyloxycarbonyl, p-methoxybenzyloxycarbonyl; (3) aliphatic urethan protecting groups such as α-t-butyloxycarbonyl, diisopropylmethoxycarbonyl, isopropyloxycarbonyl, ethoxycarbonyl, allyloxycarbonyl; (4) cycloalkyl urethan type protecting groups such as cyclopentyloxycarbonyl, adamantyloxycarbonyl, cyclohexyloxycarbonyl; (5) thiourethan type protecting groups such as phenylthiocarbonyl; (6) alkyl type protecting groups such as triphenylmethyl (trityl), benzyl; (7) trialkylsilane groups such as trimethylsilane. The preferred α-amino protecting group defined by $X^1$ is tertbutyloxycarbonyl.

$X^2$ and $X^8$ are each a protecting group for Cys or D-Cys selected from the group consisting of S-p-methoxybenzyl, S-p-methylbenzyl, S-acetamidomethyl, S-trityl, S-benzyl, and the like. The preferred protecting group is S-p-methoxybenzyl. $X^2$ and/or $X^8$ can be hydrogen which means that there is no protecting group on the sulfur group.

$X^3$ and $X^4$ are each a protecting group for the side chain amino substituent of Lys or $X^3$ and/or $X^4$ are hydrogen which means that there is no protecting group on the side chain amino substituent. Illustrative of suitable side chain amino protecting groups are benzyl, chlorobenzyloxycarbonyl, benzyloxycarbonyl, tosyl, t-amyloxycarbonyl, t-butyloxycarbonyl, etc. The selection of a side chain amino protecting group is not critical except that it must be one which is not removed during deprotection of the α-amino groups during the syntheses. Hence, the α-amino protecting and side chain amino protecting group cannot be the same.

$X^5$, $X^6$ and $X^7$ are protecting groups for the hydroxyl group of Thr and Ser and are selected from the group consisting of acetyl, benzoyl, tert-butyl, trityl, tetrahydropyranyl, benzyl, 2,6-dichlorobenzyl and benzyloxycarbonyl. The preferred protecting group is benzyl. $X^5$ and/or $X^6$ and/or $X^7$ can be hydrogen which means there is no protecting group on the hydroxyl group.

R, $R_1$, $R_2$, $R_3$, $R_4$, $R_5$, and X are as previously defined. $X^9$ is selected from the class consisting of OH, $OCH_3$, esters, amides, hydrazides and benzyl ester or hydroxymethyl ester anchoring bond used in solid phase synthesis linked to a solid resin support represented by the formulae:

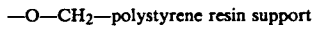
—O—$CH_2$—polystyrene resin support and

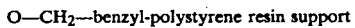
O—$CH_2$—benzyl-polystyrene resin support

The polymer is preferably a copolymer of styrene with about 0.5 to 2% divinyl benzene as a cross linking agent which causes the polystyrene polymer to be completely insoluble in certain organic solvents. In formula III at least one of $X^1$, $X^2$, $X^3$, $X^4$, $X^5$, $X^6$, $X^7$ and $X^8$ is a protecting group.

In selecting a particular side chain protecting group to be used in the synthesis of the peptides of formula I or formula II, the following rules should be followed: (a) the protecting group must be stable to the reagent and under the reaction conditions selected for removing the α-amino protecting group at each step of the synthesis, (b) the protecting group must retain its protecting properties and not be split off under coupling conditions, and (c) the side chain protecting group must be removable upon the completion of the synthesis containing the desired amino acid sequence under reaction conditions that will not alter the peptide chain.

The peptides of formula I and formula II can be prepared using solid phase synthesis. The synthesis is commenced from the C-terminal end of the peptide using an α-amino protected resin. Such a starting material can be prepared by attaching an α-amino and S-protected Cys to a chloromethylated resin or a hydroxymethyl resin. The preparation of the hydroxymethyl resin is described by Bodanszky et al., Chem. Ind. (London) 38, 1597-98 (1966). A chloromethylated resin is commercially available from Bio rad Laboratories, Richmond, California, and the preparation of such a resin is described by Stewart et al., "Solid Phase Peptide Synthesis" (Freeman & Co., San Francisco 1969), Chapter 1, pp 1–6. The α-amino and S-protected Cys is coupled to the chloromethylated resin according to the procedure of Monahan and Gilon, Biopolymer 12, pp 2513–19, 1973. Following the coupling of the α-amino and S-protected Cys to the resin support, the α-amino protecting group is removed such as by using trifluoroacetic acid in methylene chloride, trifluoroacetic acid alone or HCl in dioxane. The deprotection is carried out at a temperature between about 0° C. and room temperature.

Other standard cleaving reagents and conditions for removal of specific α-amino protecting groups may be used as described in Schroder & Lubke, "The Peptides", 1 pp 72–75 (Academic Press 1965).

After removal of the α-amino protecting group of Cys the remaining α-amino and side chain protected amino acids are coupled step-wise in the desired order to obtain a compound of formula III or as an alternate to adding each amino acid separately to the synthesis, some of them may be coupled prior to addition to the solid phase reactor. The selection of an appropriate coupling reagent is within the skill of the art. Particularly suitable as a coupling reagent is N,N$^1$-dicyclohexyl carbodiimide.

The activating reagents used in the solid phase synthesis of the peptides are those well known in the peptide art. Examples of suitable activating reagents are: (1) carbodiimides such as N,N-diisopropyl carbodiimide, N-ethyl N$^1$-(y-dimethylamino propyl carbodiimide; (2) cyanamides such as N,N-dibenzylcyanamide; (3) keteimines; (4) isoxazolium salts such as N-ethyl-5-phenyl isoxazolium-3$^1$-sulfonate; (5) monocyclic nitrogen containing heterocyclic amides of aromatic character containing one through four nitrogens in the ring such as imidazolides, pyrazolides, 1,2,4-triazolides. Specific heterocyclic amides that are useful include N,N$^1$-carbonyl diimidazole, N,N$^1$-carbonyl-di-1,2,4-triazole; (6) alkoxylated acetylene such as ethoxyacetylene; (7) reagents which form a mixed anhydride with the carboxyl moiety of the amino acid such as ethylchloroformate and isobutylchloroformate and (8) nitrogen containing heterocyclic compounds having a hydroxy group on one ring nitrogen such as N-hydroxyphthalimide, N-hydroxysuccinimide and 1-hydroxybenzotriazole. Other activating reagents and their use in peptide coupling are described by Schroder & Lubke supra, in Chapter III and by Kapoor, J. Phar. Sci., 59, pp 1–27 (1970).

Each protected amino acid or amino acid sequence is introduced into the solid phase reactor in about a fourfold excess and the coupling is carried out in a medium of dimethylformamide: methylene chloride (1:1) or in dimethylformamide or methylene chloride alone. In cases where incomplete coupling occurred the coupling procedure is repeated before removal of the α-amino protecting group, prior to the coupling of the next amino acid. The success of the coupling reaction at each stage of the synthesis is monitored by the ninhydrin reaction, as described by E. Kaiser et al., Analyt. Biochem. 34, 595 (1970).

After the desired amino acid sequence of formula III has been synthesized, the peptide is removed from the resin support by treatment with a reagent such as liquid hydrogen fluoride which not only cleaves the peptide from the resin but also cleaves all remaining side chain protecting groups X$^1$, X$^2$, X$^3$, X$^4$, X$^5$, X$^6$, X$^7$ and X$^8$ and the α-amino protecting group X$^1$ to obtain directly a peptide of formula II. Peptides in accordance with formula I are obtained by oxidizing formula II peptides in accordance with known procedures. As an alternate route, the peptide linked to the resin support may be separated from the resin by alcoholysis after which the recovered C-terminal methyl ester is converted to the acid by hydrolysis. Any side chain protecting group may then be cleaved as previously described or by other procedures such as catalytic reduction (e.g. Pd on BaSO$_4$) using conditions which will keep the Trp moiety intact. When using hydrogen fluoride for cleaving, anisole is included in the reaction vessel as a scavenger.

The solid phase synthesis procedure discussed above is well known in the art and has been essentially described by Merrifield J. Am. Chem. Soc., 85, p 2149 (1964).

The use of Phe amino acids which have been halogenated or methoxylated in the para position in accordance with the present invention provides somatostatin peptides having enhanced particular somatostatin analog with respect to inhibition of secretion of insulin and glucagon without impairment of the potency of the peptide with respect to inhibition of the secretion of growth hormone. That is, if the somatostatin peptide has a potency in comparison with somatostatin of 50% in respect to the inhibition of the secretion of growth hormone the peptides of the present invention having halogenated or methoxylated Phe amino acid moieties will also have a potency of 50 percent in respect to the inhibition of secretion of growth hormone, but the potency of the peptide in respect to the inhibition of secretion of insulin and glucagon is enhanced several fold.

Any halogen anion selected from the group consisting of chloride, iodide, bromide, and fluoride can be used in the para substituted Phe amino acid moieties. Preferred halogen anion is chloride for reasons of availability and ease of substitution. The Phe amino acids are substituted prior to attachment of the Phe amino acid to the peptide during solid phase synthesis. Any or all of the Phe amino acid moieties of the peptide can be substituted in the para position with halogen or methoxy. In a particularly preferred embodiment of the present invention all of the Phe amino acid moieties are substituted either with halogen or methoxy, but are not necessarily substituted with the same halogen or all with methoxy.

The substitution of the Phe moiety with halogen or methoxy at the para position also does not affect any dissociated activity of a somatostatin peptide. If the somatostatin peptide has dissociated activity the substitution of halogenated or methoxylated Phe does not disrupt such dissociated activity but acts to prolong the effect of the somatostatin peptide.

The following example illustrates various features of the present invention but is intended to in no way limit the scope of the invention which is defined in the appended claims.

EXAMPLE I

The peptides of the present invention were synthesized by solid phase techniques, generally in accordance with the procedure described in U.S. Pat. No. 3,904,594. The synthesis was conducted in a stepwise manner on chloromethylated resin. The resin was composed of fine beads (20–70 microns in diameter) of a synthetic resin prepared by copolymerization of styrene with one to two percent divinylbenzene. The benzene rings in the resin were chloromethylated in a Friedel-Crafts reaction with chloromethyl methyl ether and stannic chloride. The chlorine thus introduced is a reactive benzyl chloride type of linkage. The Friedel-Crafts reaction is continued until the resin contain 0.5 to 2 millimoles of chlorine per gram of resin. In the further description of the synthesis of the peptides, the reagents used will be first described by their chemical name with their common abbreviation in parenthesis. Thereafter, the reagent will be referred to by the common abbreviation.

Somatostatin for use as a control and having the structure:

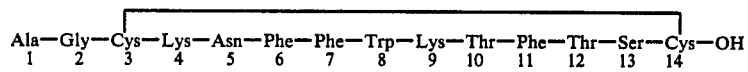

was synthesized by the following solid phase methodology. Peptides of the invention having para substituted Phe amino acid moieties, described hereinafter, were synthesized by a similar technique.

The tertiobutyloxycarbonyl-S-paramethoxybenzyl (Boc-SpOMe-Bzl) derivative of Cys was linked to the resin by any of three known methods: (1) reflux in ethanol in presence of triethyl amine, (2) Cesium salt of the Boc protected amino acid is kept at 50° C. in dimethylformamide (DMF) overnight, (3) the potassium salt of the Boc-protected amino acid is kept at 80° C. in dimethyl sulfoxide (DMSO) for 2 hours. Only one milliequivalent of the protected Cys per milliequivalent of Cl on the resin is used.

Method (3) is described hereinbelow in more detail: to a slurry of the resin and the dissolved protected Cys in DMSO is added 0.9 mEq of potassium tertiobutoxide (KOtBut) per mEq of amino acid. The reaction mixture is exposed to air as little as possible so that no amber coloration is observed. Reaction at 80° C. for 2 hours yields a suitable substituted resin for synthesis of the peptides (approx. 0.2 mEq of amino acid derivative per g of resin). After deprotection and neutralization, the peptide chain is built on the resin. Deprotection, neutralization and addition of each amino acid is performed in accordance with schedule I. Nα-t-butyloxycarbonyl (Boc derivative of each amino acid is used with the exception that any α-amino protecting group can be used for the Ala residue provided it is cleaved by HF (benzyloxycarbony; (Z) Boc and others). After deprotection of the first residue (i.e., SpOMe.Bzl. Cys) according to schedule I (steps 3 to 8 inclusive) the Nα Boc derivative of Ser is next added along with a coupling agent which is dicyclohexylcarbodiimide (DCC). (Step 9 of schedule I) The side chain of Ser is protected with benzyl ether (OBzl). The O-Benzyl (OBzl) protecting group is also used for protection of the threonine side chain. P-nitrophenyl ester (ONp) was used to activate the carboxyl end of Asn. O-nitrophenyl ester can also be used for this purpose. Formyl groups can be used for the protection of the indole N-H. Benzyloxycarbonyl (Z) or benzyloxycarbonyl-2Cl [Z (2-Cl)] was used as the protecting group for the Lys side chain.

I. Schedule for coupling of amino acids other than Asn in solid phase synthesis (5–10 g resin)

| Step | Reagents and Operations | Mix Times Min. |
|---|---|---|
| 1 | CH$_2$Cl$_2$ wash 80 ml (2 times) | 3 |
| 2 | Methanol (MeOH) wash 30 ml (2 times) | 3 |
| 3 | CH$_2$Cl$_2$ wash 80 ml (3 times) | 3 |
| 4 | 50 percent trifluoroacetic acid (TFA) containing 5 percent 1,2-ethanedithiol in CH$_2$Cl$_2$ 70 ml (2 times) | 10 |
| 5 | CH$_2$Cl$_2$ wash 80 ml (2 times) | 3 |
| 6 | Triethylamine (Et N) 12.5 percent in CH$_2$Cl$_2$ 70 ml (2 times) | 5 |
| 7 | MeOH wash 40 ml (2 times) | 2 |
| 8 | CH$_2$Cl$_2$ wash 80 ml (3 times) | 3 |
| 9 | Boc-amino acid (10 mmoles) in 10 ml DMF (1 time) and 30 ml CH$_2$Cl$_2$ plus DCC (10 mmoles) in CH$_2$Cl$_2$ (2 M) | 30 to 120 |
| 10 | MeOH wash 40 ml (2 times) | 3 |
| 11 | Et$_3$N 12.5 percent in CH$_2$Cl$_2$ 70 ml (2 times) | 3 |
| 12 | MeOH wash 30 ml (2 times) | 3 |
| 13 | CH$_2$Cl$_2$ wash 80 ml (2 times) | 3 |

After step 13, an aliquot is taken for a ninhydrin test:

If the test is negative, go back to step 1 for coupling of the next amino acid; if the test is positive or slightly positive, go back to steps 9 through 13. Schedule I was used for coupling of each of the amino acids of the peptide to Cys with the exception of Asn, when present. For peptides of the invention containing Asn, steps 1 through 8 are the same and schedule II is used for the remainder of the coupling reaction:

II. Schedule for Boc-Asn-ONp or for any active ester coupling in solid phase synthesis (5–10 g resin)

| Step | Reagents and Operations | Mix times Min. |
|---|---|---|
| 9 | DMF wash 60 ml (3 times) | 3 |
| 10 | Boc—Asn—ONp (15 mmoles) in 20 ml DMF (1 time) | 800 |
| 11 | MeOH wash 30 ml (4 times) | 3 |
| 12 | Et$_3$N 12.5 percent in DMF 30 ml (2 times) | 3 |
| 13 | MeOH wash 30 ml (2 times) | 3 |
| 14 | CH$_2$Cl$_2$ wash 80 ml (3 times) | 3 |

After step 14, an aliquot is taken for a ninhydrin test:

If the test is negative go back to step 1 for coupling of the next amino acid; if the test is positive or slightly positive, go back to steps 9 through 14.

Cleavage of the peptides from the resin (5 grams) and deprotection of the side chain protecting groups of the peptide was performed in hydrofluoric acid (75 ml) in the presence of anisole (8 ml). After elimination of hydrofluoric acid under high vacuum, the resin-peptide was washed with ether.

The dried resin was immediately extracted with 25% acetic acid (150 ml) and diluted to 3000 ml with degassed H$_2$O(N$_2$). The pH of the solution was adjusted to 6.6–7.0 with NH OH. The solution was titrated dropwise under stirring with potassium ferricyanide solution (1 g/500 ml H$_2$O) until a permanent yellow color was observed. The solution sat for 10 minutes and pH was adjusted to 5.0 with glacial acetic acid; Bio Rad Ag 30X4A resin (100–200 mesh, chloride form, 10–15 g) was added to the turbid solution and stirred for 15 minutes. The solution was filtered over celite and applied successively onto two columns; (a) Bio Rad AG 3-X4A resin chloride form (10 ml); (b) Bio Rex-70 resin (100 ml) cation form. The celite+resin cake was thoroughly washed with water (500 ml) which was applied onto columns (a) and (b) as a wash. The peptide material was then eluted from the Bio Rex-70 resin column with pyridine: acetic acid:water (30:4:66) or 50% acetic acid. Fractions were collected; only the ones containing peptide (ninhydrin positive) were diluted with water and immediately lyophilized. 1.2 g of crude cream colored material was obtained. The material was applied onto a Sephadex G-25 F gel column (3×200 cm) equilibrated and eluted with 2 N acetic acid.

The elution pattern as observed at 280 nm showed one major symmetrical peak centered at 2 Vo. It was subsequently submitted to counter current distribution (solvent system n-butanol:acetic acid:water, 4:1:5) 10 ml lower phase per tube. 237 transfers were performed and the major peak was found in tubes 46-62. The compound (250 mg) appeared homogeneous on tlc.

In vivo Bioassay: Male Sprague-Dawley-CD rats weighing 180-200 g housed in temperature and humidity controlled quarters with 14 h light and 10 h dark (light 0700-21100) were used in all experiments. Animals were fed a standard ration and tap water ad libitum. Experiments were carried out at least 5 days after arrival of rats from the supplier between the hours 1400 and 1600. After ether anesthesia, peptides or saline were administered in a volume of 0.2 ml via the external jugular vein. Animals remained anesthetized until the time of blood collection from the portal vein. Blood collection was performed at various times after administration of the peptide or saline. The blood samples were placed into chilled tubes containing 10 mg EDTA and 50 μl of 2 M Benzamidine per ml of blood.

GH determinations were performed on tissue culture media utilizing the following reagents: NIAMDD rat GH standard (GH-RP-1), NIAMDD monkey anti-rat GH (GH-Serum-3), and highly purified rat GH for iodination.

All experiments were carried on in a randomized block design. Following analysis of variance difference between treatmments were determined by the multiple range tests of Dunnett and Duncan. Potency values were calculated from four or six point bioassays.

Various peptides in accordance with the invention were prepared with the solid phase methodology described above. The composition of the peptides and their potency in comparison with somatostatin is reported hereinbelow in Table I.

RELATIVE POTENCY OF SOMATOSTATIN AND P-HALOGENATED SOMATOSTATIN ANALOGS TO INHIBIT THE SECRETION OF INSULIN, GLUCAGON AND GROWTH HORMONE

| PEPTIDE | INSULIN | GLUCAGON | GH |
|---|---|---|---|
| Somatostatin (SS) | 100 | 100 | 100 |
| [P I Phe$^{11}$]—SS | 950 | 900 | 100 |
| [P Cl Phe$^{6,7,11}$]—SS | 800 | 900 | 78 |
| [P I Phe$^{7}$]—D-Trp$^{8}$—SS | 100 | 100 | |
| [P I Phe$^{11}$]—D-Trp$^{8}$—SS | 33 | 800 | |
| Des—Asn$^{5}$—[P Cl Phe$^{6,7,11}$]—D-Trp$^{8}$—D—Ser$^{13}$—SS | 127 | >1 | |
| Des—AA$^{1,2,4,5,12,13}$—[P Cl Phe$^{6,11}$]—D-Trp$^{8}$—SS | 27 | >1 | |
| [P Cl Phe$^{6}$]—SS | 100 | 100 | |
| [P Cl Phe$^{11}$]—SS | | | |
| [P I Phe$^{6}$]—D-Trp$^{8}$—SS | 100 | 100 | |

What is claimed is:

1. A peptide selected from the group consisting of

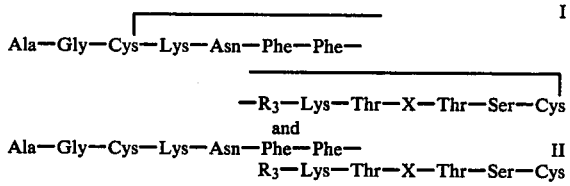

and the pharmaceutically-acceptable salts thereof, wherein

R$_3$ is selected from the group consisting of Trp and D-Trp; and

X is selected from the group consisting of parahalogenated Phe and para-methoxylated Phe.

2. A peptide in accordance with claim 1 wherein Phe in the 6-position is either para-halogenated Phe or para-methoxylated Phe.

3. A peptide in accordance with either claim 1 or claim 2 wherein Phe in the 7-position is either para-halogenated Phe or para-methoxylated Phe.

4. A peptide in accordance with claim 1 wherein X is para-iodated Phe.

5. A peptide in accordance with claim 1 wherein X is para-chlorinated Phe.

6. A peptide in accordance with claim 5 wherein Phe in the 6-position is para-chlorinated Phe, and wherein Phe in the 7-position is para-chlorinated Phe.

7. A peptide in accordance with claim 6 wherein R$_3$ is D-Trp.

8. A peptide in accordance with claim 3 wherein R$_3$ is D-Trp.

9. A peptide in accordance with claim 1 or 4 wherein R$_3$ is D-Trp.

* * * * *

UNITED STATES PATENT AND TRADEMARK OFFICE
CERTIFICATE OF CORRECTION

PATENT NO. : 4,211,693
DATED : July 8, 1980
INVENTOR(S) : Jean E. F. Rivier et al.

It is certified that error appears in the above-identified patent and that said Letters Patent are hereby corrected as shown below:

In the Abstract, formulae I and II should read as follows:

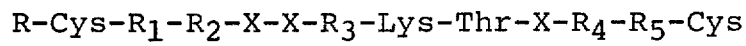

Column 3, line 15, "each of $X^1$, $X^2$ and $X^3$" should read

--each X--.

Signed and Sealed this

Twentieth Day of January 1981

[SEAL]

Attest:

RENE D. TEGTMEYER

Attesting Officer     Acting Commissioner of Patents and Trademarks